United States Patent [19]

Orr et al.

[11] Patent Number: 5,760,293

[45] Date of Patent: *Jun. 2, 1998

[54] METHOD AND APPARATUS FOR MEASURING ENVELOPE AND BULK DENSITIES

[75] Inventors: Clyde Orr, Dunwoody; Ronnie W. Camp, Duluth, both of Ga.

[73] Assignee: Micromeritics, Norcross, Ga.

[ * ] Notice: The term of this patent shall not extend beyond the expiration date of Pat. No. 5,608,157.

[21] Appl. No.: 730,924

[22] Filed: Oct. 17, 1996

Related U.S. Application Data

[63] Continuation-in-part of Ser. No. 544,591, Oct. 18, 1995, Pat. No. 5,608,157.

[51] Int. Cl.$^6$ .................................. G01N 9/00; G01F 17/00
[52] U.S. Cl. ............................. 73/32 R; 73/433; 73/149
[58] Field of Search ................................. 73/32 R, 433, 73/437, 38, 149, 823, 813, 818, 824, 825

[56] References Cited

U.S. PATENT DOCUMENTS

| | | | |
|---|---|---|---|
| 2,373,026 | 4/1945 | Guyer et al. | 73/427 |
| 2,667,782 | 2/1954 | Shea | 73/149 |
| 2,706,908 | 4/1955 | MacRoberts | 73/149 |
| 3,060,724 | 10/1962 | Smith et al. | 73/32 |
| 3,129,585 | 4/1964 | Hamilton | 73/149 |
| 3,246,504 | 4/1966 | Halff et al. | 73/32 |
| 3,309,912 | 3/1967 | Boland et al. | 73/38 |
| 3,741,011 | 6/1973 | Seybold | 73/149 |
| 4,112,738 | 9/1978 | Turner | 73/32 |
| 4,154,098 | 5/1979 | Pelletier | 73/149 |
| 4,196,618 | 4/1980 | Patterson | 73/149 |
| 4,224,821 | 9/1980 | Taylor et al. | 73/32 |
| 4,283,148 | 8/1981 | Peterson | 366/142 |
| 4,361,052 | 11/1982 | Nicol et al. | 73/863 |
| 4,699,002 | 10/1987 | Rockley | 73/153 |
| 5,323,655 | 6/1994 | Eagan et al. | 73/432.1 |

FOREIGN PATENT DOCUMENTS

| | | |
|---|---|---|
| 1959 681 | 11/1969 | Germany . |
| 42 27 376 A1 | 2/1994 | Germany . |
| 108512 | 8/1917 | United Kingdom . |
| WO 81/03547 | 12/1981 | WIPO . |

OTHER PUBLICATIONS

Chern, M.Y. et al., "Small, inexpensive apparatus for the determination of the denisty of powdered materials" *Rev. Sci. Instrum.*, vol. 61, pp. 1733–1735 (Jun. 1990).

Patent Abstracts of Japan, vol. 011, No. 015 (P-536), 16 Jan. 1987.

B. Buczek "Measurement of the Apparent Density of Porous Particles by a Powder Characteristics Tester," Proceedings of Second World Congress Particle Technology, Sep. 19–22, 1990 Kyoto, Japan, pp. 103–109.

Brochure entitled "A Tool for Solid Body Open Porosity Measurement," by Tenakon Research Industrial Corp.

ASTM Designation: C 830–83 "Standard Test Methods for Apparent Porosity, Liquid Absorption, Apparent Specific Gravity, and Bulk Density of Burned Refractory Brick and Shapes by Vacuum Pressure."

(List continued on next page.)

*Primary Examiner*—John E. Chapman
*Attorney, Agent, or Firm*—Jones & Askew

[57] ABSTRACT

A compaction device for determining envelope and bulk densities of sample materials. The device uses a rotating sample cylinder and a plunger positioned within the cylinder. The force on the plunger is measured as the plunger advances in the cylinder. The position of the plunger at which a predetermined level of force is applied thereto is determined. Envelope density is determined from the difference in the advance of the plunger when the cylinder is partially filled with a dry flowing medium and when a sample material such as a rigid object is added into the medium. Bulk density is determined from the difference in the advance of the plunger when the cylinder is empty and when the cylinder contains a sample material such as a powder.

20 Claims, 11 Drawing Sheets

OTHER PUBLICATIONS

ASTM Designation: C 493–86 "Standard Test Methods for Bulk Density and Porosity of Granular Refractory Materials by Mercury Displacement."

ASTM Designation: C 20–87 "Standard Test Methods for Apparent Porosity, Water Absorption, Apparent Specific Gravity, and Bulk Density of Burned Refractory Brick and Shapes by Boiling Water."

ASTM Designation: C 914–89 "Standard Test Method for Bulk Density and Volume of Solid Refractories by Wax Immersion."

ASTM Designation: B 527–81 "Standard Test Method for Tap Density of Powders of Refractory Metals and Compounds by Tap–Pak Volumeter".

Envelope Density Report

Date: 1/1/1996  Time: 10:11:12
Sample: CAT

| Blank Cnt | Sample Cnt | Volume   | Density   |
|-----------|------------|----------|-----------|
| 9911      | 8994       | 1.927403 | 0.7378323 |
| 10186     | 9305       | 1.851736 | 0.7679821 |
| 10207     | 9317       | 1.870653 | 0.760216  |
| 10217     | 9328       | 1.868551 | 0.761071  |
| 10220     | 9329       | 1.872755 | 0.7593627 |
| 10222     | 9336       | 1.862245 | 0.7636481 |
| 10227     | 9337       | 1.870653 | 0.760216  |

Averages that follow exclude 1st and 2nd cycle data

| | |
|---|---|
| Average envelope volume is: | 1.868971 |
| Average envelope density is: | 0.7608998 |
| Absolute (Helium) density is: | 3.5922 |
| Percent porosity is: | 78.818 |
| Maximum force was: | 10 |
| Sample weight was: | 1.4221 |
| Calibration factor used was: | 2.101857E-03 |

Bulk Density Report

Date: 1/1/1996      Time: 10:11:12

Sample: Micro-crystalline Cellulose    Sample Weight: 6.6918 g

Number of measurement cycles: 5    Number of preparation cycles: 2

Cell diameter: 25.40mm            Consolidation forces: 20.0N

| Cycle# | Blank Counts | Sample Counts | Volume (cm$^3$) | Density (g/cm$^3$) |
|---|---|---|---|---|
| 1 | 21218 | 10835 | 13.9201 | 0.4807 |
| 2 | 21216 | 10873 | 13.8665 | 0.4825 |
| 3 | 21244 | 10885 | 13.8879 | 0.4818 |
| 4 | 21239 | 10901 | 13.8598 | 0.4828 |
| 5 | 21236 | 10887 | 13.8745 | 0.4823 |

Average bulk volume: 13.8818 cm$^3$    Standard deviation: 0.0238
Average bulk density: 0.4820 g/cm$^3$   Standard deviation: 0.0008

METHOD AND APPARATUS FOR MEASURING ENVELOPE AND BULK DENSITIES

RELATED APPLICATIONS

This application is a continuation in part of application Ser. No. 08/544,591, filed on Oct. 18, 1995, entitled "Method and Apparatus for Measuring Envelope Densities," now U.S. Pat. No. 5,608,157.

TECHNICAL FIELD

The present invention relates to a method and apparatus for measuring the density of one or more objects, and more particularly, to an automated device for determining the envelope density of objects and the bulk density of powders.

BACKGROUND OF THE INVENTION

The density of an object is defined as its mass per unit volume (d=m/v). Density is generally stated in terms of grams per cubic centimeter or pounds per cubic foot. The mass of an object is easily established with a balance. The volume of an object is also easily determined if the object is an impervious solid of simple geometric shape. For example, the volume of a cube is the edge length cubed ($L^3$).

Envelope Density

Determining the volume of an object of complex shape or an object with holes or pores can be difficult and involve time-consuming measurement techniques. Further, the volume of the object is a matter of definition. The volume of an object can be determined by either excluding the volume of the holes and the pores to find its absolute density (also termed the true or skeletal density) or including the holes and pores up to the point at which they break the plane of the surface to determine the envelope density (also called the bulk or apparent density). Absolute density can be determined by compressing the object until all of the voids are eliminated and only a continuous solid phase remains or by a pycnometer employing helium gas that penetrates the pores of the object.

One aspect of the present invention is directed towards determining the envelope density of rigid, porous objects. Common rigid, porous objects include everything from sugar cubes and aspirin tablets to floor tiles, concrete, and bakery cookies. Other examples include oil well cores (after the liquid therein is expelled), catalyst pellets, and sintered metal bearings and gears.

The envelope density of an object is valuable when used in conjunction with its absolute density to determine the porosity of that object and its specific pore volume (i.e., the pore space that was eliminated upon compression):

Porosity=[(1−Envelope Density/Absolute Density)100] %

Pore Volume=[1/Envelope Density−1/Absolute Density] cm$^3$/g

Porosity and pore volume are parameters that frequently establish the fitness of an object for its intended purpose.

Until recent years, the most widely used technique for assessing external volume involved submerging the test object in mercury and measuring the displaced liquid volume. Testing of this type is described in ASTM Standard Test Method C493-93, entitled "Bulk Density and Porosity of Granular Refractory Materials by Mercury Displacement." Mercury is a non-wetting fluid that bridges the pore entrances and does not penetrate small cracks, holes, or pores. The use of mercury, however, is being phased out because of health concerns. The sample object also becomes contaminated by contact with mercury and must be treated as a hazardous waste.

Another known method requires the sample object to be boiled in water and then remain submerged while the water cools and fills the pores. The sample is first weighed dry, then weighed while suspended in water, and weighed after superficial drying to obtain the desired information. This testing method is described in ASTM Standard Test Method C20-92, entitled "Apparent Porosity, Water Absorption, Apparent Specific Gravity, and Bulk Density of Burned Refractory Brick and Shapes by Boiling Water." A related procedure, ASTM Standard Test Method C830-93, substitutes evacuation for boiling in water and then fills the pores with water or mineral spirits. Both of these methods are tedious and require considerable operator skill to dry the exterior surface of the object while keeping the pores filled with the liquid.

A further method seals off the pores of an object by dipping the object in melted paraffin wax. The wax is not supposed to fill the pores but to seal off the pore entrances. The dry weight, the wax-coated weight in air, and the wax-coated weight suspended in water are used to determine the envelope density. See ASTM Standard Test Method C914-89, entitled "Bulk Density and Volume of Solid Refractories by Wax Immersion." This method is also tedious and can destroy the usefulness of the object because the coating may be impractical to remove.

Attempts have been made in the past to measure the envelope density of an object with the use of dry materials. An example includes British Patent No. 108,512 in which the envelope density of a loaf of bread is determined by filling a container with turnip seeds both with and without the bread present. The envelope density of the loaf is defined as the difference in the volume of the turnip seeds present in the container in both tests. Another method is described in German Patent No. 1,959,681 in which the interior volume of a complex cast iron mold cavity is determined. The cavity is filled with a free flowing powder of known density and then the powder is weighed to determine the cavity volume.

Similar methods include the determination of envelope density of bits of silica gel, carbon, and other particles by placing the particles in a container and filling the container and an extension of it with a fine powder of bronze, steel or zinc. The container and extension are then vibrated vertically and the contents compacted. The extension is removed and the volume of the sample particles is determined by measuring the mass of the powder filling the container with and without the particles present. Results are dependent upon the vigor of the vibration, the excess mass of the powder in the cup extension, and the manual skill of the operator in removing the excess powder.

Finally, the Research and Industrial Corporation of Russia, "TENAKON," describes a device entitled "A Tool for Solid Body Open Porosity Measurement." TENAKON describes a method by which a sample is placed on a vertically moveable piston positioned within a cylinder. A free flowing powder of some sort is then dumped on top of the sample. The cylinder is capped with a cover containing an electrical interrupter switch. The piston moves up and presumably compresses the free-flowing powder until the piston drive is interrupted. No attempt is made to distribute the material around the sample. The volume confined within the cylinder defines the volume of the sample once the free-flowing powder volume is subtracted. It is understood that such a device may be accurate for flat-bottomed sample materials, but not particularly accurate for crushed or irregular objects.

What is needed, therefore, is a method and apparatus for the measurement of envelope density that provides reliable, reproducible results. These results should be superior to those found with the use of other fluids or known dry medium methods and should not require tedious sample manipulation. The method and apparatus must be easy to use, employ non-hazardous materials, and be non-destructive to the object being tested.

Bulk Density

Bulk density is a parameter of value in determining how granular, fibrous or powdery materials pack or consolidate under a variety of conditions. Although not an inherent property of the material, the measurement is of use in packaging, handling and shipping all manner of products from breakfast cereals to cement. For example, the bulk density of "filler" powders is an important parameter used in the manufacture of items such as flooring tiles, plastic products, and pharmaceuticals. This density measurement is often referred to as "tap" density because known apparatus for its measurement are mechanical devices that alternately lift and drop a container of the subject material a number of times, producing a loud tapping noise.

This testing method is described in ASTM Standard Test Method B 527-81, "Tap Density of Powders of Refractory Metals and Compounds by Tap-Pak Volumeter." The tap density of a given material is determined by filling a container of known volume with a known mass of the material and then vibrating or dropping the container a number of times. The volume of the material is then determined by measuring the height of the material within the container along a vertical scale. The value determined by the tapping-type of apparatus depends upon the vigor of tapping, the number of taps and the height of the bed of material initially placed in the container.

There is also a need, therefore, for a method and apparatus for the measurement of bulk density that provides reliable and reproducible results. The method and apparatus should be able to quantify the densities of a wider range of materials than possible with known means.

SUMMARY OF THE INVENTION

Generally described, the present invention provides a compaction device for determining envelope and bulk densities of sample materials. The device uses a rotating sample cylinder and a plunger positioned within the cylinder. The force on the plunger is measured as the plunger advances in the cylinder. The position of the plunger at which a predetermined level of force is applied thereto is determined. Envelope density is determined from the difference in the advance of the plunger when the cylinder is partially filled with a dry flowing medium and when a sample material such as a rigid object is added into the medium. Bulk density is determined from the difference in the advance of the plunger when the cylinder is empty and when the cylinder contains a sample material such as a powder.

In a preferred embodiment, the rotation of the sample cylinder includes rapid forward and reverse agitation. The compaction means includes a plunger driven by a stepper motor with a threaded drive shaft. The means for detecting the position of the compaction means comprises counting the number of steps input to the stepper motor. Alternatively, the compaction means could use a DC motor with an associated encoder and then count the number of counts produced by the encoder. The means for measuring the force on the compaction means includes a load cell.

The invention also includes envelope density control means for determining the difference in the number of steps input to the stepper motor both with a dry flowing medium placed within the sample cylinder and with a dry flowing medium and one or more objects placed within the sample cylinder. The control means then multiplies the difference in the number of steps input to the stepper motor by the number of threads per a predetermined length of the threaded drive shaft, the drive ratio between the stepper motor and the threaded drive shaft, and the cross-sectional area of the sample cylinder so as to determine the volume of the one or more objects. The control means then divides the known mass of the one or more object by the determined volume so as to determine the envelope density of the one or more objects.

The invention further includes bulk density control means for determining the difference in the number of steps input to the stepper motor to reach a predetermined force both with and without an amount of sample material placed within the sample cylinder. The control means then multiplies the difference in the number of steps input to the stepper motor both with and without the sample material by the number of threads per a predetermined length of the threaded drive shaft, the drive ratio between the stepper motor and the threaded drive shaft, and the cross-sectional area of the sample cylinder so as to determine the volume of the sample material. The control means then divides the known mass of the sample material by the determined volume so as to determine the bulk density of the sample material.

Other objects, features, and advantages of the present invention will become apparent upon review of the following detailed description of the preferred embodiment of the invention, when taken in conjunction with the drawings and the claims.

DETAILED DESCRIPTION OF THE INVENTION

The Apparatus

Figure 1:
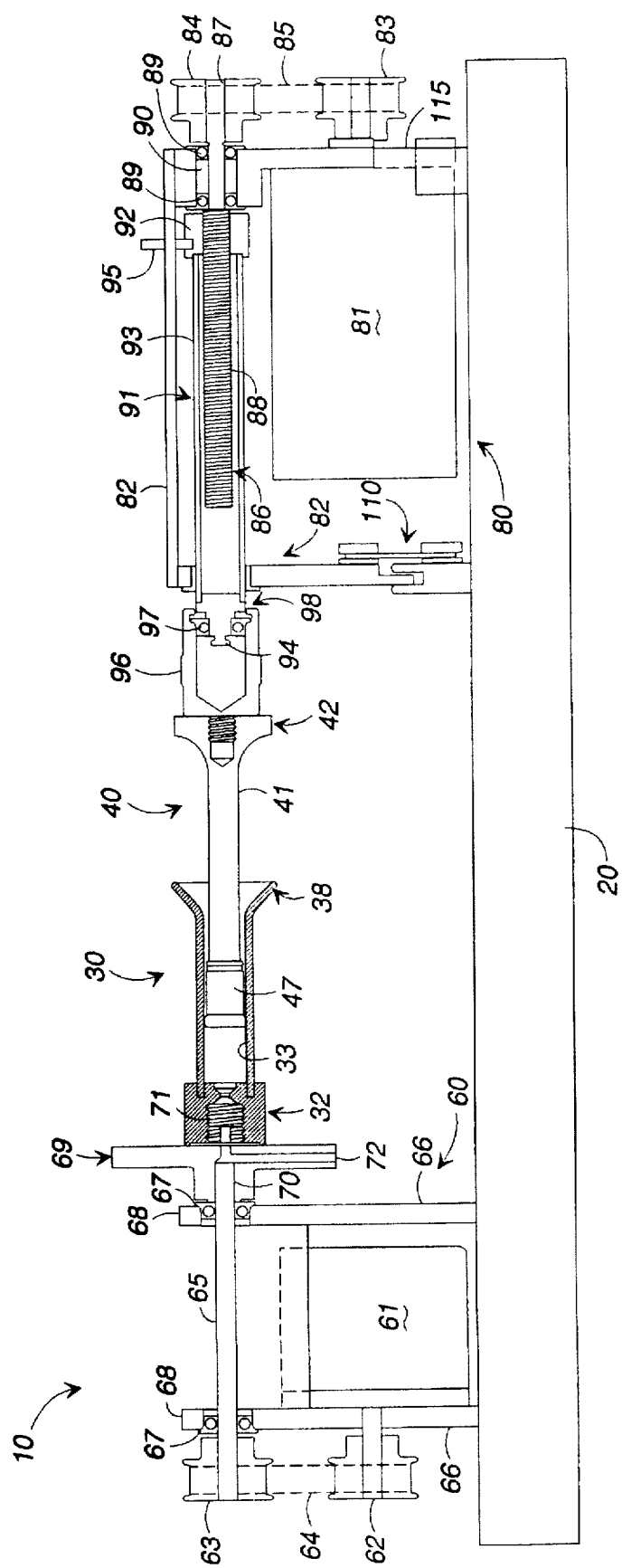
FIG. 1 is a side view showing an envelope density measurement apparatus embodying the invention.
Figure 2:
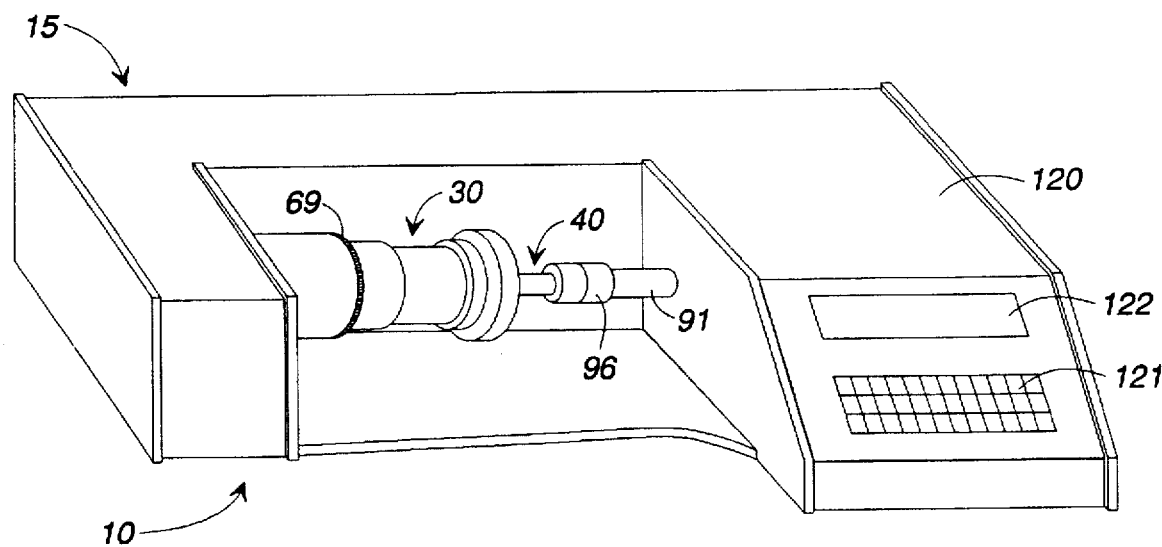
FIG. 2 is a perspective view of a commercial embodiment of the envelope density measurement apparatus.
Figure 3:
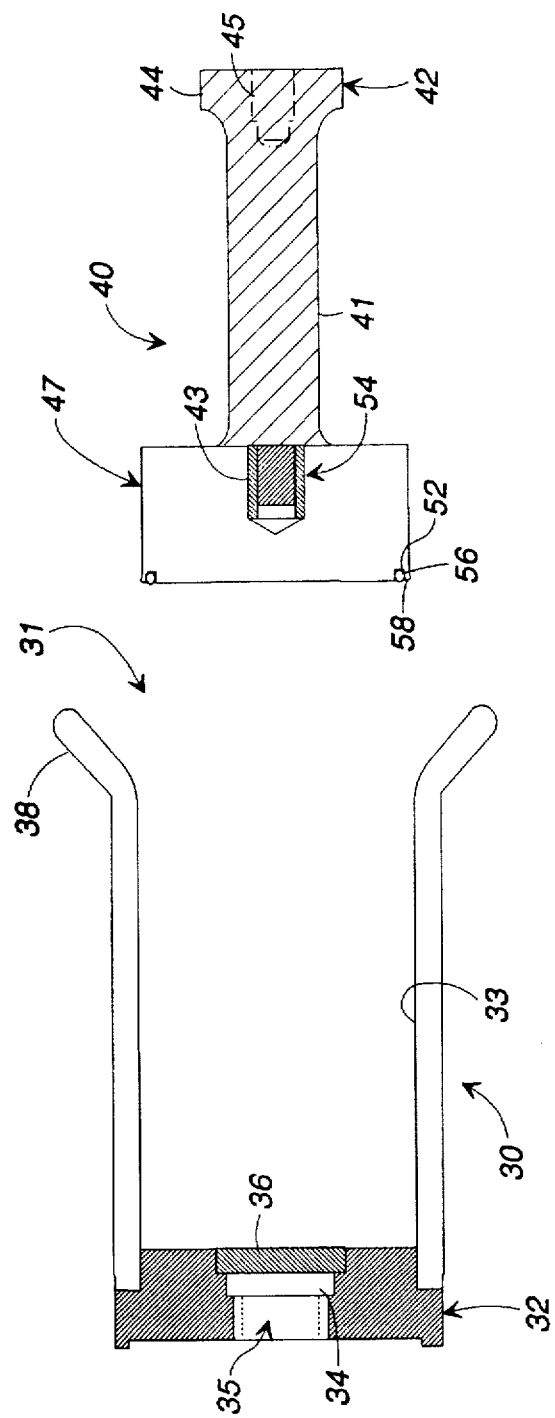
FIG. 3 is a side cross-sectional view of the cylinder and the plunger of FIG. 1.

Referring now in more detail to the drawings in which like numerals refer to like parts throughout the several views, FIGS. 1–3 show a density apparatus 10 embodying the present invention. Generally described, the apparatus 10 includes a support base 20, a sample cylinder 30, a plunger 40, a rotating motor assembly 60, a drive motor assembly 80, a load cell 110, and a control means 120. In a commercial embodiment of the apparatus 10, these parts and assemblies may be contained in a housing 15 as shown in FIG. 2. The apparatus 10 is used to determine the envelope density of one or more porous objects 140 or the bulk density of powdered, fibrous, or granular materials 142. The porous objects 140 and the granular, fibrous or powdery materials 142 are collectively referred to as sample material 145.

Referring to FIGS. 1 and 3, the sample cylinder 30 is preferably constructed with a precision-bore glass tube. Borosilicate glass is preferably used. The inside diameter of the sample cylinder 30 is preferably consistent within 0.1%. The sample cylinder 30 has an open end 31, a cap 32 enclosing the other end, and a polished interior wall or surface 33. The cap 32 has an opening 34 within the cylinder 30 and a center hole 35 outside of the cylinder 30. The cap 32 is preferably made from stainless steel and is cemented or otherwise fixedly attached to the cylinder 30. A porous plate 36 fills the opening 34 of the cap 32. The porous plate 36 is preferably a flat sintered metal disc. The cap 32 also acts as a vent to allow the passage of air out of the cylinder 30 when the plunger 40 is extended therein.

The open end 31 of the cylinder 30 preferably extends into a funnel-like shape 38. The funnel 38 aids in pouring the medium 130 and/or the sample material 145 in and out of the cylinder 30. The funnel 38 is preferably an integral part of the cylinder 30. Alternatively, a funnel-shaped member may be fixedly attached to the cylinder 30.

The glass-walled cylinder 30 permits viewing the interior thereof and is an advantage when filling or emptying the cylinder 30 or positioning the sample material 145 therein. Any conventionally sized cylinder 30 may be used, with cylinder 30 diameters of ½ inch, ¾ inch, 1 inch, 1-½ inch, and 2 inches preferred. The length of the cylinder 30 is preferably approximately three times the diameter. The dimensions of the cylinder 30 and the plunger 40 will vary and preferably be sized according to the size of the sample material 145.

The plunger 40 for use with a one inch diameter cylinder 30 is shown in FIG. 3. The plunger 40 comprises a stem 41 with an enlarged end 42 at one end and a reduced diameter threaded post 43 at the other. The stem 41 is preferably made from 304 or 316 stainless steel. The threaded post 43 is preferably made from 360 brass. The enlarged end 42 has a flange 44 with a knurled exterior surface and a threaded central bore 45.

A piston head 47 is mounted at the post end of the stem 41. The piston head 47 is a unitary piece with a circumferential channel 52 on one end and a threaded aperture 54 at the other end. The piston head is preferably made from Teflon. A quad-ring 56 is inserted into the circumferential channel 52. The quad-ring 56 is preferably made from an elastic material of approximately 70 durometer. The threaded aperture 54 receives the threaded post 43 of the stem 41. The piston head 47 also has an integral flange 58 adjacent to circumferential channel 52. The flange 58 is angled slightly away from the enlarged end 42 of the stem 41. An angle of approximately 4.5 degrees is preferred. The quad-ring 56 ensures that the flange 58 stays expanded and in contact with the cylinder walls 33.

The cylinder 30 is mounted for axial rotation to the rotating motor assembly 60. The rotating motor assembly 60 includes a drive motor 61 mounted to rotating motor assembly support frame 66 by conventional means. The support frame 66 extends upwardly from the base 20. The motor 61 drives a lower timing pulley 62 that, in turn, powers an upper timing pulley 63 via a timing belt 64. The upper timing pulley 63 is mounted on a drive shaft 65. The drive shaft 65 is mounted in a collinear position with respect to the cylinder 30 and the plunger 40. The drive shaft 65 is preferably made from stainless steel. The drive shaft 65 rotates within a pair of bearings 67 packed within retaining rings 68. The retaining rings 68 are mounted on support frame 66 by conventional means.

The drive shaft 65 is connected at the end opposite the upper timing pulley 63 to a wheel-shaped grip 69. The wheel-shaped grip 69 has an aperture 70 on one end for mating with the drive shaft 65 and a hollow, threaded member 71 on the other end for mating with the center hole 35 of the cap 32 of the cylinder 30. The drive shaft 65 mates with the aperture 70 via a set pin (not shown) or other conventional means. The wheel-shaped grip also may include a radial vent hole 72 extending outwardly from the hollow threaded member 71. The radial vent hole 72 communicates with the porous plate 36 of the cap 32 of the cylinder 30 to permit the escape of air from the cylinder 30 as the plunger 40 advances therein. The wheel-shaped grip 69 also has a knurled surface to assist in gripping and turning the grip 69. The wheel-shaped grip 69 is preferably made from 304 or 316 stainless steel.

The rotating motor assembly 60 agitates the cylinder 30 in precession-like fashion by rotating x degrees in one direction and then y degrees in the reverse direction, preferably where x>y. The preferred rotation is for the cylinder 30 to rotate 45 degrees in one direction, reverse 30 degrees in the other direction, and then to repeat this procedure. The drive motor 61 is preferably a stepping motor such as that sold under the trademark "SLO-SYN" by Superior Electric, or a DC motor. The motor 61 preferably rotates the cylinder 30 at approximately 25 rpm and should be capable of quickly reversing direction to produce high accelerations. Other types of manual or mechanical devices can provide the preferred rotation of the cylinder 30.

The plunger 40 is preferably screw driven by the drive motor assembly 80. The drive motor assembly 80 includes a drive motor 81 mounted to a drive motor support frame 82 by conventional means. The support frame 82 extends upwardly from the base 20. The drive motor 81 drives a lower timing pulley 83 that, in turn, drives an upper timing pulley 84 via a timing belt 85. The upper timing pulley 84 is attached by conventional means to a threaded shaft 86. The threaded shaft 86 has a journaled end 87 adjacent to the upper timing pulley 84 and an opposite threaded end 88. The journaled end 87 is mounted in bearings 89 packed within retaining rings 90. The retaining rings 90 are mounted on the support frame 82 by conventional means. The threaded end 88 of the shaft 86 has a preferred pitch of approximately 6.297 threads per centimeter. The threaded shaft 86 is preferably made from 303 stainless steel. There is preferably about a 3 to 1 drive ratio between the motor 81 and threaded shaft 86.

The threaded shaft 86 is positioned within a drive shaft 91. The drive shaft 91 has a threaded ring 92 on the end adjacent to the upper timing pulley 83, an extended hollow cylinder 93, and an enclosed, extended male member 94. The threaded ring 91, the hollow cylinder 93, and the male member 94 are connected via welding or other conventional means or may be formed as an integral piece. The threaded ring 92 has an interior diameter and a pitch to match the diameter and pitch of the threaded end 88 of the shaft 86. The threaded ring 92 has a stop pin 95 extending therefrom. The stop pin 95 rides within a slot (not shown) within the support frame 82 to prevent the drive shaft 91 from rotating. The drive shaft 91 moves horizontally in and out as driven by the threaded shaft 86.

The extended male member 94 of the drive shaft 91 is connected to a bearing bracket 96 via bearings 97. The bearing bracket 96 has a female end 98 and an extended threaded post 99. The bearings 97 are packed in the female end 98 of the bearing bracket 96. The threaded post 99 is attachable to the threaded central bore 45 of the stem 41 of the plunger 40. The bearing bracket 96 is preferably made from 304 or 316 stainless steel. The drive shaft 91 can exert axial force on the plunger 40 via the bearing bracket 96 while the cylinder 30 rotates with the rotating motor assembly 60.

The drive motor 81 may be a stepping motor, such as that sold under the trademark "SLO-SYN" by Superior Electric. A stepping motor 81 of 200 steps per revolution may be used. Alternatively, a DC motor with an associated encoder (not shown) may be used. How far the drive shaft 91 and hence the plunger 40 advances or withdraws is determined by the steps input to the drive motor 81 in combination with the known pitch of the threaded shaft 86 and the drive ratio between the motor 81 and the threaded shaft 86. The advance or retraction of the shaft 86 and the plunger 40 is measured to the nearest 0.000359 centimeter. Other types of manual and mechanical compacting means may be employed.

Mounted to the drive motor assembly support frame 82 is a thin beam load cell 110. The assembly support frame 82 is also supported by two flexible support members 115. The support members 115 are made from thin, flat spring steel. Force exerted upon the plunger 40 through the threaded shaft 86 is thus transmitted to the load cell 110 and the two flexible support members 115. The flexible support members 115 offer negligible resistance to the force in the direction the force is applied, leaving the load cell 110 itself to resist the force. The applied force causes the load cell 110 to bend slightly into an "S" shape which changes its electrical resistance and creates the applied force signal. Other types of manual and mechanical measuring means may be employed.

The Control Means

The operation of the drive motors 61, 81 and the load cell 110 are monitored and controlled by the control means 120. The control means 120 has a Central Processing Unit ("CPU") (not shown) that is a conventional microprocessor. The control means 120, a key pad 121 to accept the various inputs, and a display 122 for the appropriate information. All information will be available by the control means 120 in English, German, French, Spanish, Italian, and other common languages. A printer or RS-232 data channel (not shown) also may be used.

Figures 7, 9A:
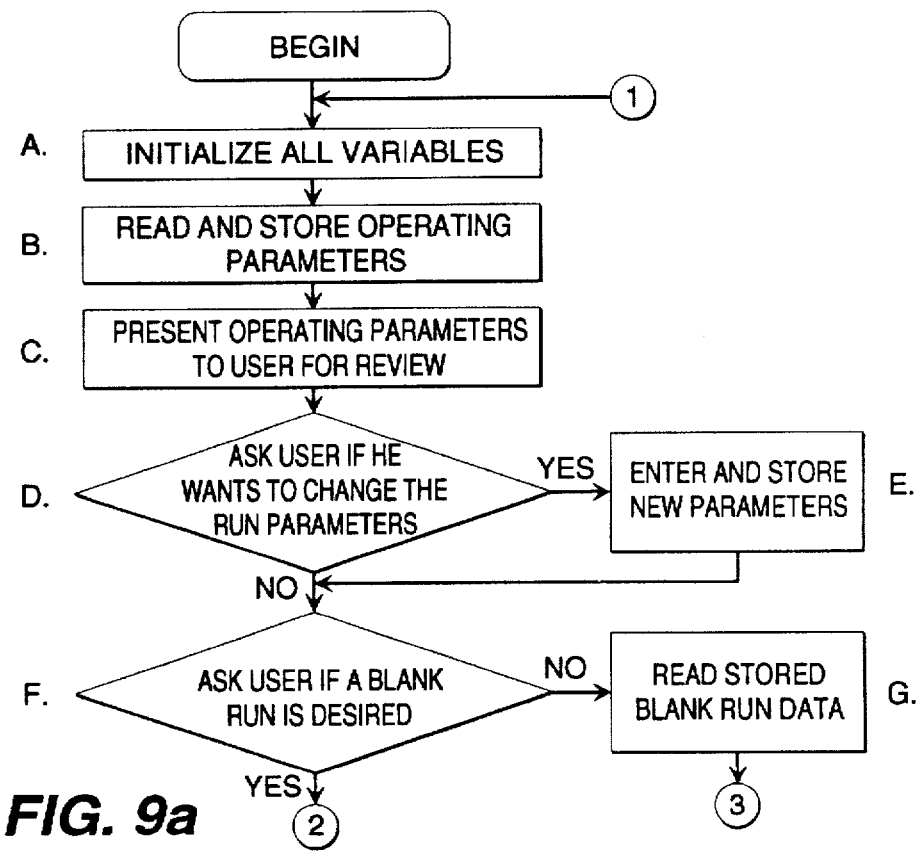
FIG. 7 is a sample envelope density run report.
Figure 9B:
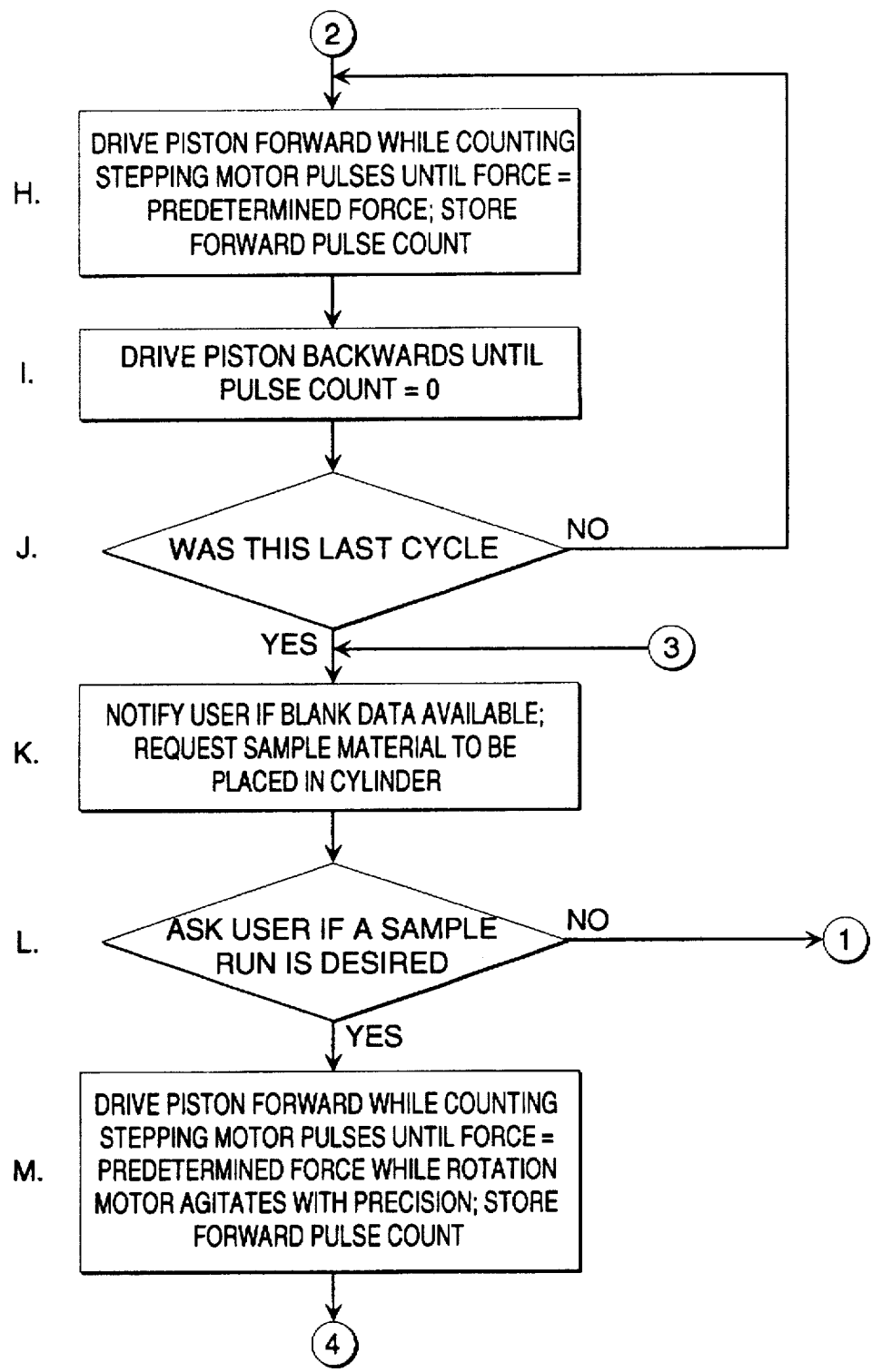
FIG. 9 is a flow chart showing the bulk density processing steps of the apparatus.
Figure 9C:
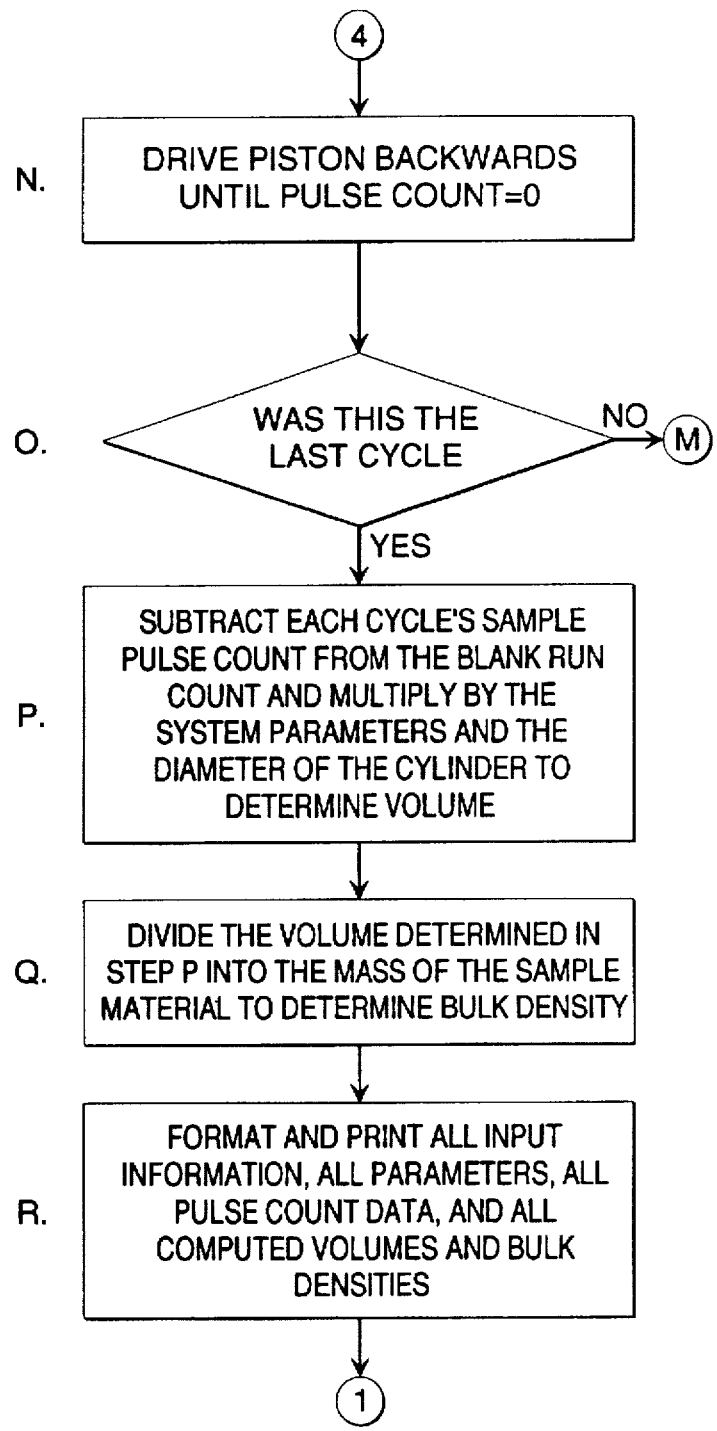

In the preferred embodiment, the system software is coded in the C+ programming language. Detailed flow charts of the preferred operations of the apparatus 10 as performed by the control means 120 are shown in FIGS. 7 and 9. As an analogy to an electrical circuit diagram, these flow charts are equivalent to a detailed schematic for an electrical circuit where provision of the circuitry for electrical circuit blocks corresponds to provision of actual computer instructions for blocks of the flow chart. Thus, the coding of the process steps of these flow diagrams into instructions for suitable commercially available computers is within the capability of one skilled in the art of programming.

The Dry Flowing Medium

Figure 4:
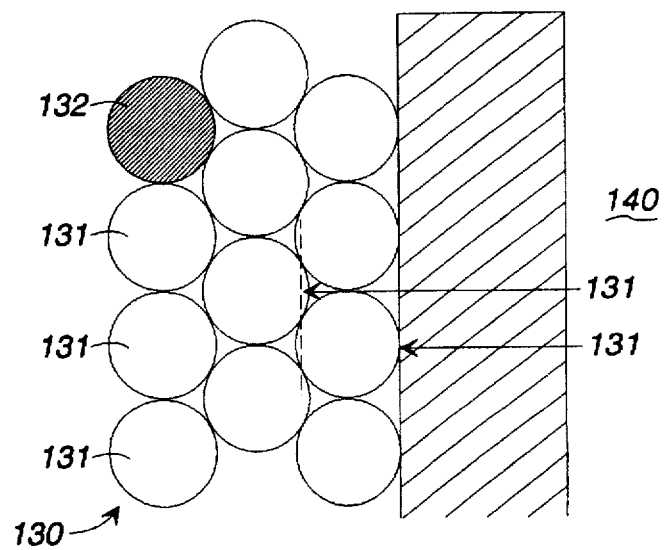
FIG. 4 is a side cross-sectional view of the beads comprising a bed of a dry flowing medium.
Figure 5:
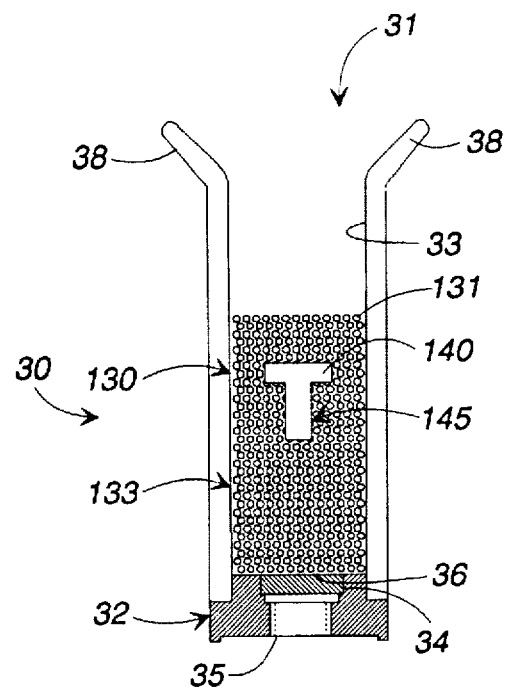
FIG. 5 is a side cross-sectional view of the cylinder with a dry flowing medium (exaggerated) and a sample object therein.

As is shown in FIGS. 4–5, a dry flowing medium 130 is used in the cylinder 30 in determining the envelope density of sample porous objects 140. Although a dry medium undergoing compaction does not transmit forces equally in all directions as does a liquid, the use of uniform, small diameter spheres 131 in connection with agitation and stepwise compaction can produce accurate results. The dry flowing medium 130 is preferably a plurality of small, rigid beads 131. Glass, metal, ceramic, plastic or other spherical materials also may be used as the beads 131. These materials generally do not contaminate or destroy the porous object 140. The beads 131 may be hollow depending upon the weight of the material used. The beads 131 are mixed with a flow inducing agent such as graphite 132. The graphite 132 adheres to the bead surface with no dustiness. Some of the graphite 132 also coats the walls 33 of the cylinder 30 and the cup seal 51 of the plunger 40. The dry flowing medium 130 can be reused for multiple tests.

Beads 131 of various sizes and coarseness can be used depending upon the size and nature of the sample object 140. The size of the pores in the object 140 also should be considered in determining the size of the beads 131 to be used. Beads 131 ranging from about 40 to 250 µm may be used. A dry flowing medium 130 with a specific gravity of about 0.7 is recommended when the object 140 is lightweight or of low envelope density such as with catalyst substrates and insulating materials. A dry flowing medium 130 with a specific gravity of about 2.5 may be used when testing heavier objects or objects with a high envelope density such as metallic and metal-containing objects.

As is shown in FIG. 4, the first layer of beds 131, whatever the bead size, creates an envelope around the porous object 140. The smaller the diameter of the beads 131, the closer the beads 131 can conform to the shape of the porous object 140. This increased conformity should lead to increased accuracy because larger diameter beads 131 can neither closely outline the periphery of the porous object 140 nor conform to minor indentations in its surface. Because of van der Waals forces, however, compact formation, i.e., cakes of beads 131 that form when compressed under forces generated by the plunger 40, becomes more pronounced and the compacts become more difficult to disperse as bead diameter decreases. The formation of compacts is detrimental to measurement because the formation indicates rigidity in the bed 133 and the inability of the beads 131 to conform to the shape of the objects within the bed 133.

The objective in choosing bead size, therefore is to choose bead sizes that are as small as possible with acceptable flow characteristics. Nearly uniform-sized glass beads 131 of approximately 100 µm in diameter exhibit good flow characteristics, in that they do not give rise to compacts, and give accurate measurements when a proper calibration factor is used.

Envelope Density Operation

The principle upon which the apparatus 10 operates is to confine and consolidate a quantity of the dry flowing medium 130 within the cylinder 30 and then measure the volume of the medium 130. The dry flowing medium 130 is consolidated within the cylinder 30 while undergoing agitation until the predetermined force is reached. The consolidation force applied via the plunger 40 is then released and the porous object 140 (or objects) is inserted into the dry flowing medium 130. Consolidation is again achieved with agitation and the new volume is measured. The difference in the two volumes is taken as the volume of the porous object 140. Multiple tests or "cycles" of both blank and sample runs are preferred for statistically meaningful results. By consolidating the dry flowing medium 130, backing the plunger 40 off a few counts to loosen the medium 130 slightly, advancing the plunger 40 again to consolidate the medium 130 to a further degree, and repeating these steps, the subject invention provides highly reproducible results.

Specifically, how far the plunger 40 moves in terms of driving motor steps or counts until the predetermined force is reached is measured in both a "blank" run and in a sample run. The volume of the porous object 140 is computed from the difference in the steps of the motor 81 in light of the cross-sectional area of the cylinder 30 and the mechanical parameters inherent in driving the plunger 40 with drive motor assembly 80. For example, if the plunger 40 is driven by the motor 81 that registers 200 counts per revolution with the threaded shaft 86 having 6.297 threads per centimeter, and a 3 to 1 drive motor ratio between the motor 81 and threaded shaft 86, and if d is the diameter of the cylinder, the default volume (v) equivalent to one count of the motor 81 is:

$$v = |\pi d^2/((200)(4)(6.297)(3))| \text{ cm}^3/\text{count}. \qquad [\text{Eqn. (1)}]$$

The default envelope volume (V) of the porous object 140 is then the difference in the counts with the sample present ($C_{present}$) and with it absent ($C_{absent}$) multiplied by v or:

$$V = |(C_{present} - C_{absent}) v| \text{ cm}^3. \qquad [\text{Eqn. (2)}]$$

The apparatus 10 runs three types of tests, a calibration run, a blank run and a sample run. Because, as described above, the dry flowing medium 130 is not quite an ideal fluid, irregular objects in the bed 133 produce small distortions in the internal forces produced within the cylinder 30. The influence of these distorted internal forces can be largely nullified by calibration with another object having known properties and of approximately the same shape as the porous object 140. The calibration object (not shown) is usually a nonporous object because the envelope and absolute densities are identical. If the porous object 140 to be analyzed is truly of unique shape, it may be necessary to fabricate a nonporous calibration object of similar shape. When a calibration test is made with a nonporous sample of known volume V, the above Equation (2) is solved for v. This value of v then becomes the corrected conversion factor for the blank and sample runs.

Finding an object or objects suitable for calibration purposes is generally not difficult. For example, some catalysts are spherical in shape such that glass or plastic spheres provide a satisfactory calibration object. If the catalysts are in the form of short extrudates, broken glass or plastic rods are satisfactory. Crushed rock or brick pieces are adequately simulated by broken bits of glass. Pharmaceutical tablets and pills can be calibrated by using glass spheres of the same approximate size.

The next step in conducting a test is to choose the appropriately sized cylinder 30 and fill it with the appropriate amount and type of dry flowing medium 130. If enough beads 131 are not employed, the porous object 140 itself will prevent bed compaction. If too many beads 131 are used, the uniformity of the compaction of the bed 133 may be compromised. The porous object 140 preferably should constitute at least about one-third of the volume of the final compacted bed 133. Similarly, the cylinder 30 must be of sufficient size to provide the greatest possible shift of the plunger 40 between the blank and sample tests.

It is preferred that the porous object 140 be centrally positioned within the beads 131 rather than against one end of the cylinder 30. If more than one porous object 140 is being tested at one time, the objects should be uniformly spread throughout the bed 133. Unlike with vertical rotation where heavy objects tend to position themselves on the bottom of the cylinder 30, porous objects 140 heavier than the beads 131 generally position themselves centrally in the bed 133 as the cylinder 30 rotates horizontally. Less dense porous objects 140 readily become submerged within the bed 133 as the test proceeds. If the porous object 140 has a large central hole, it is best to position the axis of the hole along the axis of the cylinder 30 to ensure compaction of the beads 131 within the hole.

Among the several procedures for conducting a test, the most reliable is to make a blank test and then immediately repeat the test with the porous object 140. This assures that the bed 133 is identical in both cases. As described above, the greatest accuracy is achieved when the apparatus 10 is first calibrated with a calibration object of known properties and having the appropriate size and shape of the porous object 140. The calibration sample is then removed from the bed 133 and the beads 131 are returned to the bed 133 to assure that the force patterns for the blank and sample runs are the same as the calibration run. It is satisfactory to calibrate the apparatus 10 once with a calibration sample and then use approximately the same quantity of identical beads 131 in subsequent tests.

The blank test can be dispensed with if nearly the same bed weight is used in every test and a number of preliminary blank tests covering the possible range of bed weights is made. This data can be stored in the control means 120. Storing the preliminary blank run data and interpolating for the exact weight of each subsequent bed weight may be performed by the control means 120. The composition of the bed should preferably remain the same if a mixture of bead 131 sizes is being used. This may require repeated stirring of the bead mix. The bed weighing procedures should preferably be accurate within 1 milligram to give reproducible results.

A constant force of compaction should preferably be employed in any series of tests in conformity with the requirement for consistency in a procedure. The influence of force on test results is not strong but significant. A force of 2 to 4 pounds is generally applicable with the ½ inch diameter cylinder 30, 10 to 15 pounds is appropriate for the 1 inch cylinder 30, and 25 to 35 pounds should normally be employed for the 2 inch diameter cylinder 30. Applied forces on the bed 133 of these magnitudes are not fully transmitted to the porous object 140 within because some force is used in overcoming the "stiction" force or the force needed to cause the plunger to move while in contact with the walls 33 of the cylinder 30. The additional force needed to overcome the stiction force is added to the entered compaction force. Although distortions are generally not caused to ordinary porous objects 140 during testing, fragile objects should be tested for damage to determine if a reduced force level is necessary.

A constant number of cycles should also be used. Although the first few compaction cycles are likely to be widely variable, the tests thereafter are generally consistent. The present system is programmed to disregard the first few trials. This means that at least three test cycles should be employed. A total of five to seven cycles is preferred to give accurate measurements and a fair calculation of standard deviation.

Care should be taken that no beads 131 are lost in inserting or removing the porous object 140. After the media 130 or the media 130 and porous object 140 are positioned in the cylinder 30, the cylinder 30 is positioned such that the plunger 40 is partially inserted therein. The central hole 35 of the cap 32 of the cylinder 30 is then mated with the threaded member 71 of the wheel-shaped grip 69 of the rotating motor assembly 60. The cylinder 30 is removed by reversing this process. The plunger 40 may also be removed by unscrewing the stem 41 of the plunger 40 from the threaded post 99 of the bearing bracket 96.

Figure 6A:
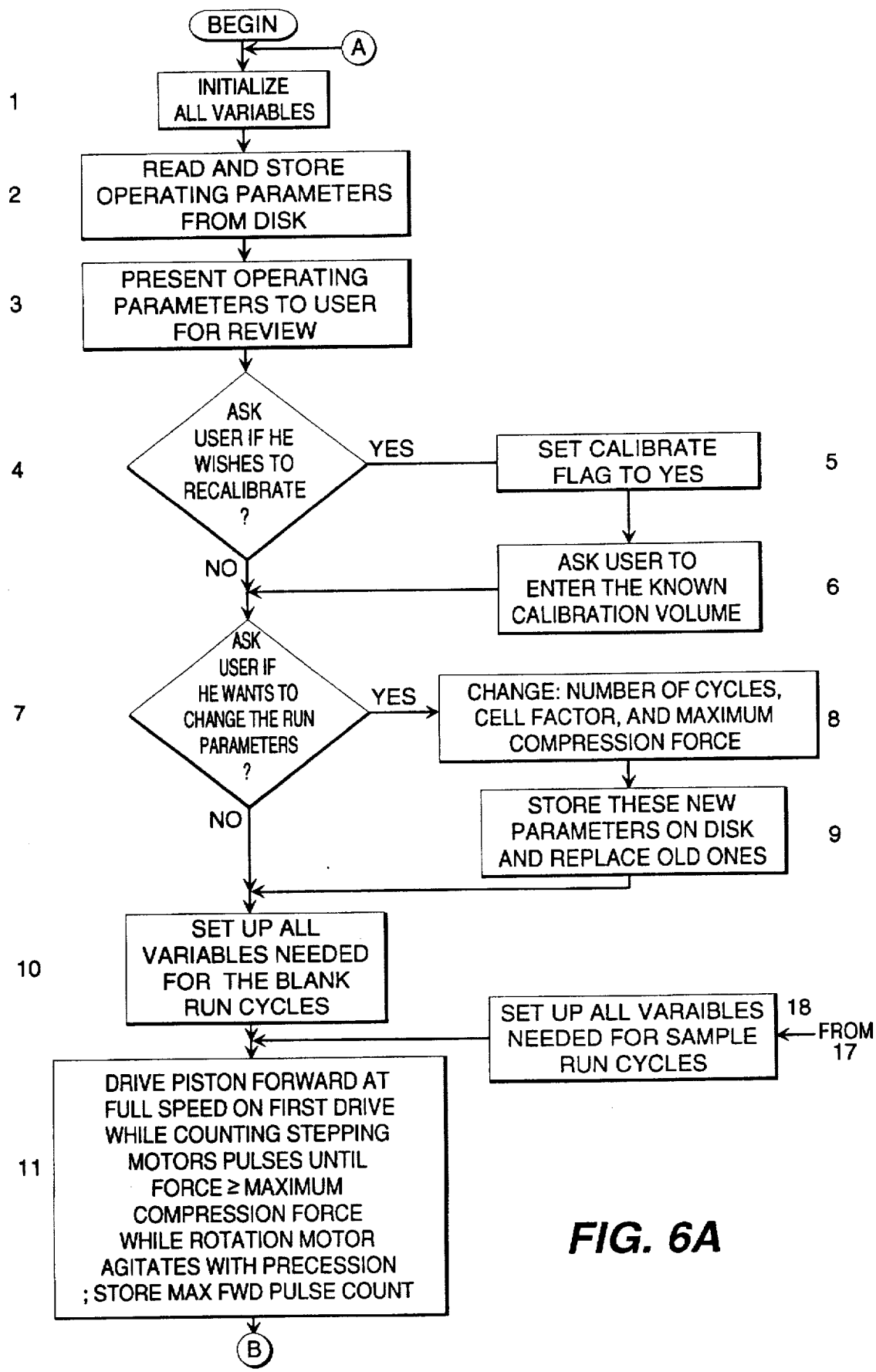
FIG. 6 (A)–(C) is flow chart showing the envelope density processing steps of the apparatus.
Figure 6B:
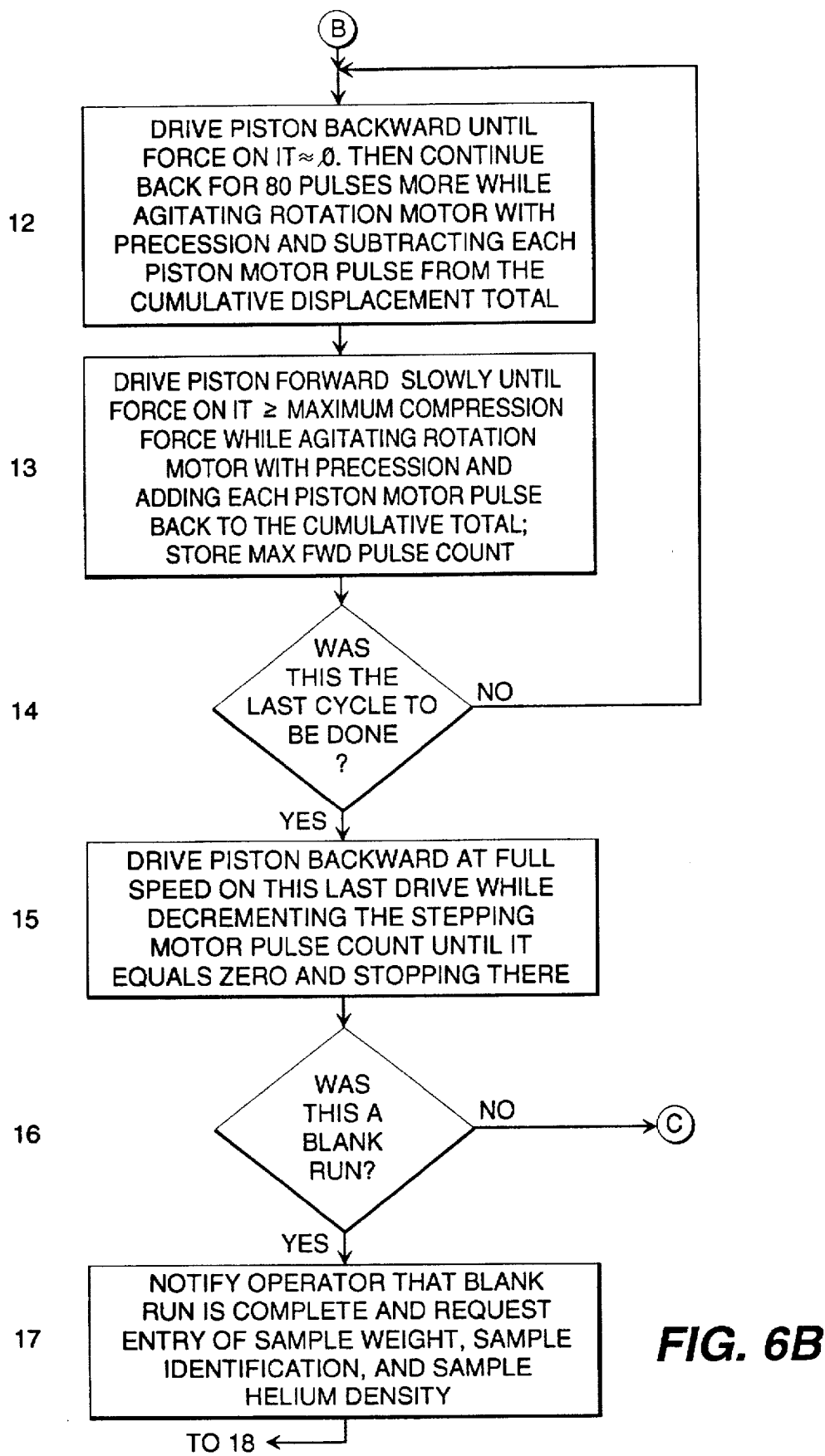
Figure 6C:
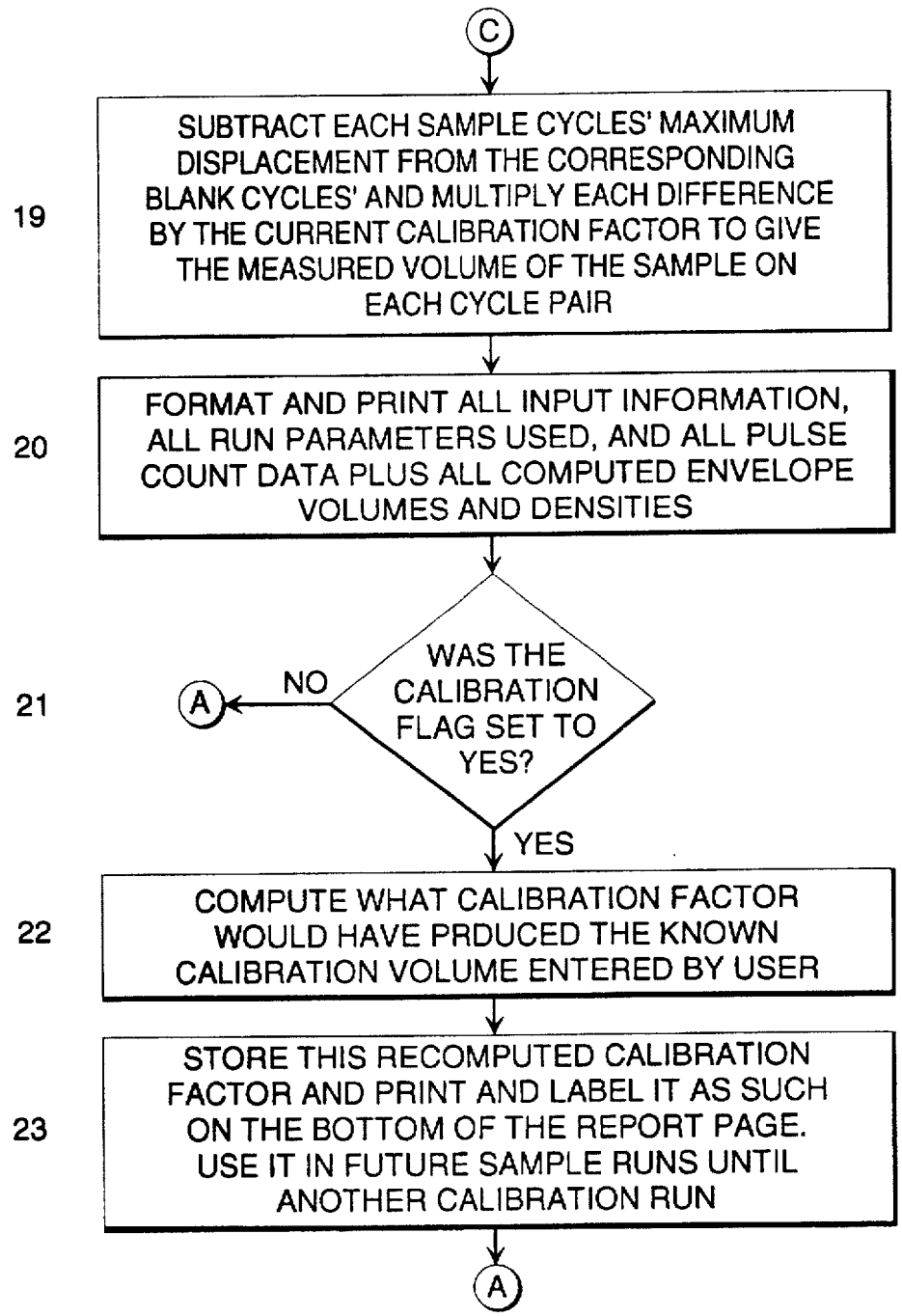

Referring now to the flow charts of FIG. 6. Steps 1 through 10 involve establishing the appropriate variables for the run. The control means 120 initializes all appropriate variables in step 1 and then reads and stores the operating parameters in step 2. In step 3, the control means 120 presents these parameters to the user for review on the display 122. The operating parameters include run precision in terms of percentage and the maximum number of cycles. Meaningful statistical information usually requires 5 cycles, although any number of cycles between 1 and 25 may be entered. Other run parameters include the amount of consolidation force to be applied in terms of pounds or Newtons and the calibration factor in terms of cubic centimeters per count.

In step 4, the control means 120 then asks the user if the apparatus 10 is to be re-calibrated. If the user indicates yes, the calibration flag is set to "yes" in step 5 and the control means 120 asks the user for the known calibration volume of the calibration sample in step 6. In step 7, the control means 120 asks the user if the run parameters are to be changed. If the user indicates yes, the user can change, as described above, the number of cycles to be run, the calibration factor, and the maximum compression force in step 8. These parameters are then stored in the control means 120 in step 9. The control means 120 then sets all variable required for a blank run in step 10.

In step 11, the apparatus 10 begins operation. The motor 61 of the rotating motor assembly 60 continually agitates the cylinder 30. The motor 81 of the drive motor assembly 80 drives the plunger 40 forward while the drive motor 81 steps are accounted for by the control means 120. The plunger 40 compacts the dry flowing medium 130 until the predetermined maximum compression force is reached as measured by the load cell 110 at which time the control means 120 stops the motor 81. The maximum forward pulse count of the motor 81 is maintained by the control means 120. In step 12, the plunger 40 is then backed up until the force thereon as determined by the load cell 110 equals zero pounds. The plunger 40 is then withdrawn an additional 80 pulses of the stepper motor 81, or approximately 0.3 mm further. Each stepper motor 81 pulse used to withdraw the plunger 40 is then subtracted from the maximum forward pulse count. The control means 120 maintains the cumulative displacement pulse total. The rotating motor assembly 60 continues to agitate the cylinder 30 while the plunger 40 is withdrawn to permit dilation of the bed 133, or to allow the bed 133 to expand and the individual beads 131 to rearrange their respective positions. This completes one cycle.

In step 13, the plunger 40 is then slowly advanced into the cylinder 30. The plunger 40 is again advanced until the force on the plunger 40 is equal to the predetermined pressure force as measured by the load cell 110. The maximum forward pulse count is again determined and stored in the control means 120. The rotating motor assembly 60 continues to agitate the cylinder 30 during this step. As is shown in step 14, the cycle (steps 12 and 13) is repeated until the maximum number of cycles as input by the user is reached. In step 15, the plunger 40 is again withdrawn until the load thereon reaches zero if the maximum number of cycles has been reached. The number of steps input by the motor 81 are again counted by the control means 120 and subtracted from the cumulative total.

In step 17, if this run was a blank run, the user is notified that the blank run is complete and the control means 120 then requests entry of the weight of the porous object 140,
porous object 140 identification, and porous object 140 absolute density. These variables are again set in step 18 and steps 11 through 16 are repeated using the sample.

If this was not a blank run, the maximum displacement of each cycle is subtracted from the corresponding blank cycles in step 19. The number of blank cycles should be equal to the maximum number of sample consolidation cycles. Each such sum is then multiplied by the current calibration factor, as in Equation (2), to give the measured volume of the porous object 140 on each cycle pair. In step 20, all input information, run parameters, pulse count data, and all computed envelope volumes and densities are formatted and printed. If the absolute density of the object 140 was entered, the percentage porosity will also be printed. FIG. 7 is a sample run report.

In step 21, if the calibration flag was set, the calibration factor (v) is computed using Equation (2) based upon the known calibration volume entered in step 22. This information is then stored in step 23 and is used as (v) in Equation (2) until the next calibration run.

Envelope Density Results

The typical error from true volume for measurements taken of porous objects 140 by the method described above with approximately 100 µm diameter beads 131 is less than approximately plus or minus two percent. When a calibration object that adequately represents the form and other significant features of the unknown porous object 140 is used, however, the typical resulting error after calibration will be reduced to approximately plus or minus one percent. "Typical" as used here shall mean that over fifty percent of the measurements made on arbitrary selected sample materials will exhibit errors under the stated limit. The repeatability of measurements taken through successive cycles is generally plus or minus one percent Repeatability depends, in part, upon the size of the cylinder 30 and the volume of the sample object 140. Although the preferred diameter of the beads 131 appears to be approximately 100 µm, different sizes or even combinations of various sized beads 131 may give superior results depending upon the shape of the sample object 140.

Bulk Density Operation

Figure 8:
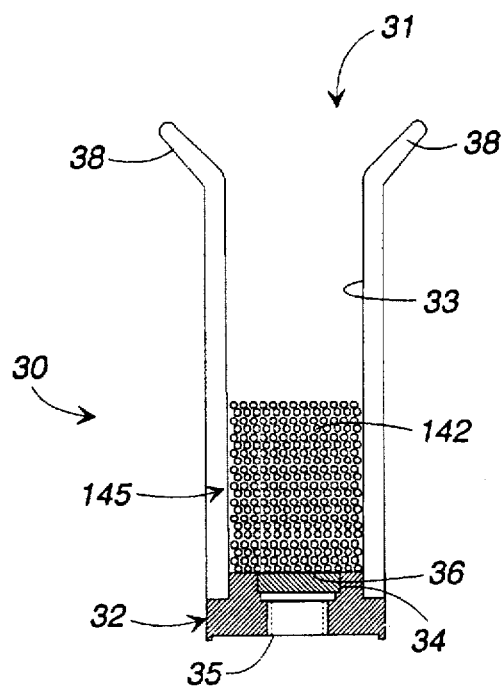
FIG. 8 is a side cross-sectional view of the cylinder with an amount of material (exaggerated) therein.

The principle upon which the apparatus 10 operates to determine bulk density is to confine and consolidate a quantity of the sample material 142 within the cylinder 30 as is shown in FIG. 8. The material 142 is consolidated within the cylinder 30 by the plunger 40. The distance traveled by the plunger 40 into the cylinder 30 until a predetermined force on the plunger 30 is reached is then compared to the distance traveled by the plunger 40 when the cylinder 30 is empty, i.e., a blank run, until that same force is reached. The material 142 is generally agitated during compaction. Multiple tests or "cycles" of both blank and sample runs are preferred for statistically meaningful results.

Specifically, how far the plunger 40 moves in terms of drive motor steps or counts until a predetermined force is reached is measured in both a "blank" run and in a sample run. The volume of the sample material 142 is computed from the difference in the steps of the motor 81 in light of the cross sectional area of the cylinder 30 and the mechanical parameters inherent in driving the plunger 40 with the drive motor assembly 80. In the example of Eqn. (1) described above, the default volume(v) is based upon the motor 81 having 200 counts per revolution, the threaded shaft 86 having 6.297 threads per centimeter, a 3 to 1 drive motor ratio between the motor 81 and the threaded shaft 86, and D as the diameter of the cylinder. The bulk volume ($V_B$) of the sample material 142 is the difference in the counts with the sample material 142 present ($C_{present}$) and with it absent ($C_{absent}$) multiplied by v, or:

$$V_B = [(C_{present} - C_{absent})\, v]\ cm^3. \qquad [\text{Eqn. (3)}]$$

The bulk density of the sample material 142 is then determined by dividing the known mass of the sample material 142 by the determined bulk volume. ($D_B = m/V_B$)

In making a blank run. the distance traveled by the plunger 40 within the cylinder 30 until the plunger 40 asserts a predetermined amount of force on the cap 32 of the cylinder 30 is determined and stored by the control means 120. The blank run may be repeated for a series of different forces. The blank run data may be stored in the control means 120 and used for a multiplicity of future tests or discarded and redone each time a sample is to be tested.

The cylinder 30 is filled with an appropriate amount of the sample material 142. The compacted length of the sample material 142 preferably should be no more than the diameter of the cylinder 30. but may be more or less. The plunger 40 is again advanced into the cylinder 30 and compacts the material 142 until the predetermined force is reached. The apparatus 10 agitates the cylinder 30 to assist in the consolidation of the sample material 142. The control means 120 calculates the difference between these results and the stored blank run data described above. Preferably, the same number of blank cycles and sample cycles are run.

Referring now to the flow chart of FIG. 9. the control means 120 initializes all appropriate variables in step A and then reads and stores the operating parameters in step B. In step C. the control means 120 presents these parameters to the user for review on the display 122. The operating parameters include the number of cycles to be run and the predetermined force to be applied in terms of Newtons. As before, meaningful statistical information usually requires at least five cycles, although any number of cycles between 1 and 20 may be entered. In step D, the control means 120 asks the user if the run parameters are to be changed. If so, the new parameters are entered and stored in step E.

In step F, the control means 120 asks the user whether a blank run is desired or whether stored blank data is available to be used. If the user indicates that stored data is to be used, the control means 120 reads and brings forth the appropriate data in step G. In step H, if the user chooses to make a blank run, the apparatus 10 begins operation. The motor 81 of the drive motor assembly 80 drives the plunger 30 forward from a predetermined starting point where the motor 81 pulse count is zero. The control means 120 counts the pulses of the drive motor 81 as the plunger 30 advances. The plunger 40 advances until it contacts the cap 32 of the cylinder 30 with the predetermined force as measured by the load cell 110. The control means 120 then stops the motor 81. The maximum forward pulse count of the motor 81 is maintained by the control means 120. In step I, the plunger 40 is returned to the predetermined starting point where the pulse count is zero. This completes one cycle. As is shown in step J, this process is repeated until the maximum number of cycles is reached.

In step K, the control means 120 notifies the operator that the blank run is complete and requests that the sample material 142 be placed in the cylinder 30. In step L, the control means 120 then asks the user whether to start a sample run. If the user indicates yes, the apparatus 10 again begins operation. The motor 81 of the rotating motor assembly 60 continually agitates the cylinder 30 during compaction. In step M, the motor 81 of the drive motor assembly 80 again drives the plunger 40 forward from the predetermined starting point while the drive motor pulses are accounted for by the control means 120. The plunger 40 compacts the sample material 142 until the predetermined maximum force is again reached. The maximum forward pulse count of the motor 81 is again maintained by the control means 120. In step N, the plunger 40 is again returned to the predetermined starting point where the pulse count is zero. This completes one cycle. As is shown in step O, the cycle is repeated until the maximum number of cycles as input by the user is reached. The number of sample cycles and all other operating conditions should be the same as those of the blank cycles.

Figures 10, 11:
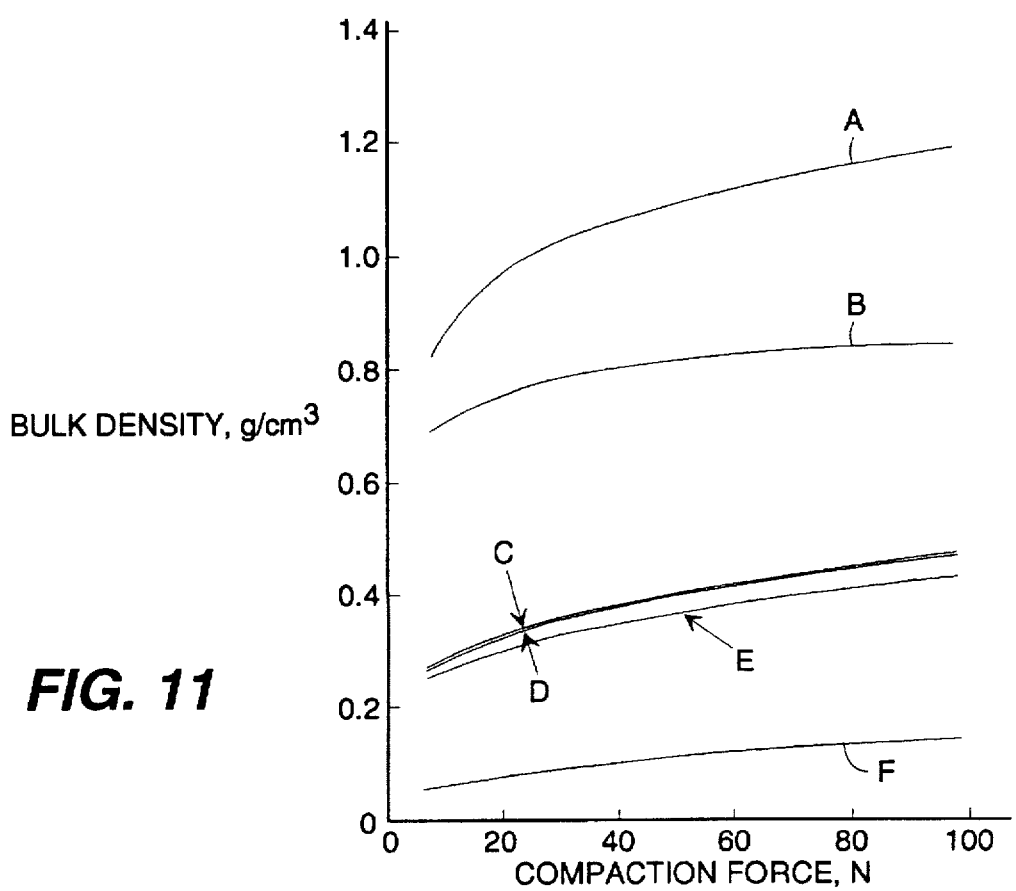
FIG. 10 is a sample bulk density run report.
FIG. 11 is a packing behavior graph.

In step P, the volume of the sample material 142 for each cycle is determined by subtracting each cycle's sample pulse count from the corresponding blank run count and multiplying this figure by the appropriate system parameters and the diameter of the cylinder 30 as described above. In step Q, the bulk density of the sample material 142 is determined by dividing the volume as determined in step P into the known mass of the sample material 142. In step R, all input information, run parameters, pulse count data, and all computed bulk volumes and densities are formatted and printed. FIG. 10 is a sample run report.

Bulk Density Results

The user may select the appropriate degree of force that corresponds to the number of "taps" used to collect past data. Alternatively, measurements may be made over a range of force values to yield additional information about the packing behavior of the sample material 142. It is to be expected that bulk densities increase as the consolidation forces increase. Determined bulk densities are typically identical to tap densities between consolidation forces of 10 to 15 Newtons, when applied with a plunger 30 of about 5.07 $cm^2$ in size (i.e., consolidation of about 2-3 Newtons per $cm^2$).

For example, a comparison test was made with an amount of perlite material having a tap density of 0.068 $g/cm^3$. The apparatus 10 determined the following bulk densities with the given consolidation forces:

| Force | Bulk Density in $g/cm^3$ |
|---|---|
| 5N | 0.0627 |
| 10N | 0.0660 |
| 15N | 0.0680 |
| 20N | 0.0708 |

FIG. 11 is a graph showing the change in bulk density of various materials at increasing compaction forces. A cylinder of 25.4 mm in diameter is used. The graph also shows how various materials compact when mixed together. Line A is talc USP, line B is lactose, line C is magnesium stearate, impalpable powder, line D is magnesium stearate, line E is a mixture of 96.5 percent magnesium stearate and 3.5 percent silica (by weight), and line F is fumed silica. As is shown, the mixture of certain materials may provide a more flowable substance than the original material. For example, the addition of an amount of fumed silica to the magnesium stearate powder apparently "opens up" the spaces among the grains of the powder, thereby making the mixture more flowable and decreasing the bulk density of the mixture as a whole.

Bulk densities of materials composed of rigid granules are not significantly altered by harder pressing and more vigorous shaking. These materials seem to give consistent bulk density values almost regardless of test conditions. More bulky materials yield values more dependent upon actual test conditions. This invention permits a wide range of forces and agitation conditions to be applied unlike the tap density procedures where all conditions are arbitrarily fixed.

The foregoing relates only to the preferred embodiments of the present invention, and many changes may be made therein without departing from the scope of the invention as defined by the following claims.

We claim:

1. A compaction device, comprising:

a hollow sample cylinder of known interior diameter;

means for rotating said hollow sample cylinder;

compaction means comprising a stepper motor and a threaded drive shaft, said compaction means removably positioned within said hollow sample cylinder for advancement therein;

means for measuring the force on said compaction means as it advances in said hollow sample cylinder;

means for detecting the position of said compaction means in said hollow sample cylinder at which a predetermined level of force is applied thereto, said means comprising counting the number of steps input to said stepper motor; and control means for:
determining the difference in the number of steps input to said stepper motor with and without a sample material placed within said hollow sample cylinder;
multiplying said difference in the number of steps input to said stepper motor both with and without said sample material placed within said hollow sample cylinder by the number of threads per a predetermined length of said threaded drive shaft, the drive ratio between said stepper motor and said threaded drive shaft, and the cross-sectional area of said hollow sample cylinder so as to determine the volume of said sample material placed within said hollow sample cylinder; and
dividing the mass of said sample material by said volume so as to determine the bulk density of said sample material.

2. A compaction device, comprising:

a hollow sample cylinder of known interior diameter;

means for rotating said hollow sample cylinder;

compaction means comprising a stepper motor and a threaded drive shaft, said compaction means removably positioned within said hollow sample cylinder for advancement therein;

means for measuring the force on said compaction means as it advances in said hollow sample cylinder;

means for detecting the position of said compaction means in said hollow sample cylinder at which a predetermined level of force is applied thereto, said means comprising counting the number of steps input to said stepper motor; and control means for:
determining the difference in the number of steps input to said stepper motor with a dry flowing medium placed within said hollow sample cylinder and with a dry flowing medium and one or more objects placed within said hollow sample cylinder;
multiplying said difference in the number of steps input to said stepper motor both with a dry flowing medium placed within said hollow sample cylinder and with a dry flowing medium and one or more objects placed within said hollow sample cylinder by the number of threads per a predetermined length of said threaded drive shaft, the drive ratio between said stepper motor and said threaded drive shaft, and the cross-sectional area of said hollow sample cylinder so as to determine the volume of said one or more objects placed within said hollow sample cylinder; and
dividing the mass of said one or more objects by said volume so as to determine the envelope density of said one or more objects.

3. An apparatus for measuring the bulk density of an amount of material of known mass, comprising:

a hollow sample cylinder of known interior diameter;

a plunger removably positioned within said hollow sample cylinder;

said plunger mounted to a stepper motor for movement within said hollow sample cylinder;

a load cell connected to said plunger to measure the force on said plunger as it advances in said hollow sample cylinder; and control means responsive to said load cell for:
determining the number of steps input to said stepper motor when a known force is exerted on said plunger both when said hollow sample cylinder is empty and when said amount of material is positioned within said hollow sample cylinder; and
calculating the volume of said amount of material by determining the difference between said number of steps input to said stepper motor and dividing said volume into said mass of said amount of material.

4. The apparatus for measuring the bulk density of an amount of material of known mass of claim 3, wherein said hollow sample cylinder is mounted to a motor for forward and reverse agitation.

5. The apparatus for measuring the bulk density of an amount of material of known mass of claim 3, wherein said stepper motor comprises a threaded drive shaft.

6. The apparatus for measuring the bulk density of an amount of material of known mass of claim 5, wherein said control means determines said volume of said amount of material by multiplying said difference in said steps input to said stepper motor, both with and without said amount of material present therein, by the number of threads per a predetermined length of said threaded drive shaft, the drive ratio between said motor and said threaded drive shaft, and the cross-sectional area of said sample cylinder.

7. A method for determining the bulk density of an amount of material of known mass, comprising the steps of:

advancing a plunger within a cylinder of known interior diameter;

measuring the advance of said plunger within said cylinder until a first known force is placed on said plunger;

withdrawing said plunger;

placing said amount of material into said cylinder;

advancing said plunger within said cylinder;

measuring the advance of said plunger within said cylinder with said amount of material positioned therein until said first known force on said plunger is reached;

calculating the difference between said advance of said plunger in said cylinder with and without said amount of material positioned therein so as to determine the volume of said amount of material and dividing this sum into said mass of said amount of material.

8. The method of claim 7, further comprising the step of rotating said cylinder in forward and reverse directions after said step of placing said amount of material into said cylinder.

9. The method of claim 7, wherein said plunger is advanced by a stepping motor and wherein said steps of measuring said advance of said plunger comprise measuring the steps input to said stepper motor.

10. The method of claim 7, further comprising multiple testing cycles wherein each said cycle comprises said steps of measuring said advance of said plunger in said cylinder, both with and without said amount of material therein, and calculating said differences.

11. The method of claim 7, further comprising the steps of measuring the advance of said plunger within said cylinder until a second known force is placed on said plunger, both with and without said amount of material positioned therein; and calculating said difference between said advance of said plunger in said cylinder with and without said amount of material positioned therein at said second known force so as to determine the volume of said amount of material, whereby the packing behavior of the material may be assessed.

12. The method of claim 7, further comprising multiple testing cycles wherein different known forces are placed on said plunger and wherein each testing cycle comprises said steps of measuring said advance of said plunger in said cylinder, both with and without said amount of material therein, and calculating said differences.

13. An apparatus for measuring the bulk density of an assemblage of objects of known weight comprising:

a hollow sample cylinder of known interior diameter;

said hollow sample cylinder mounted to a motor for rotation about its horizontal axis;

said assemblage of objects positioned within said hollow sample cylinder;

a plunger removably positioned within said hollow sample cylinder;

said plunger mounted to a drive motor for axial movement within said hollow sample cylinder to consolidate said assemblage of objects;

a load cell connected to said plunger to measure the force on said plunger as it advances in said hollow sample cylinder; and control means responsive to said load cell for:

determining the position of said plunger in said hollow sample cylinder at which a known force is exerted on said plunger; and calculating the volume of said assemblage of objects and dividing said volume into said weight of said assemblage of objects so as to determine the bulk density of said assemblage of objects.

14. The bulk density measurement apparatus of claim 13, wherein said rotation of said hollow sample cylinder comprises rapid forward and reverse agitation.

15. The bulk density measurement apparatus of claim 13, wherein said plunger has an outer seal comprising polytetrafluorethylene.

16. The bulk density measurement apparatus of claim 13, wherein said hollow sample cylinder comprises vent means for the escape of air from said cylinder as said plunger advance therein.

17. The bulk density measurement apparatus of claim 13, wherein said drive motor comprises a stepper motor.

18. The bulk density measurement apparatus of claim 17, wherein said drive motor comprises a threaded drive shaft.

19. The bulk density measurement apparatus of claim 18, wherein said means for detecting the position of said plunger in said hollow sample cylinder at which a predetermined force is applied thereto comprises counting the number of steps input to said stepper motor.

20. The bulk density measurement apparatus of claim 19, wherein said control means for calculating the volume of said assemblage of objects in said hollow sample cylinder comprises multiplying said difference in the number of steps input to said stepper motor both with and without said assemblage of objects placed within said hollow sample cylinder by the number of threads per a predetermined length of said threaded drive shaft, the drive ratio between said stepper motor and said threaded drive shaft, and the cross-sectional area of said hollow sample cylinder.

\* \* \* \* \*